United States Patent
Mergy et al.

(10) Patent No.: US 6,919,557 B2
(45) Date of Patent: Jul. 19, 2005

(54) DEVICE FOR CONTINUOUS MOVEMENT OF OBJECTS WITH SYMMETRY, USE FOR VISUAL INSPECTION AND CONTROL

(75) Inventors: Marc Mergy, Boulogne (FR); Jean-Luc Lecomte, Albert le Petit (FR); Laurent Letellier, Paris (FR); Jean-François Larue, Voiron (FR)

(73) Assignee: Compagnie Generale des Matieres Nucleaires, Velizy-Villacoublay (FR)

( * ) Notice: Subject to any disclaimer, the term of this patent is extended or adjusted under 35 U.S.C. 154(b) by 0 days.

(21) Appl. No.: 10/169,853

(22) PCT Filed: Oct. 8, 2001

(86) PCT No.: PCT/FR01/03462
§ 371 (c)(1),
(2), (4) Date: Aug. 18, 2003

(87) PCT Pub. No.: WO02/38474
PCT Pub. Date: May 16, 2002

(65) Prior Publication Data
US 2004/0035680 A1 Feb. 26, 2004

(30) Foreign Application Priority Data
Nov. 9, 2000 (FR) .......................................... 00 14410

(51) Int. Cl.[7] .............................................. G01V 8/00
(52) U.S. Cl. ............................ 250/223 R; 250/559.42; 250/559.46; 356/446; 356/430; 356/237.3; 198/839; 414/431; 209/576
(58) Field of Search ........................... 356/237.2, 237.3, 356/445, 446, 429–431, 238.1, 238.2, 239.1, 239.5; 250/223 R, 223 B, 559.4–559.46; 198/415, 839; 414/431; 209/576

(56) References Cited

U.S. PATENT DOCUMENTS

| | | | | |
|---|---|---|---|---|
| 4,185,921 A | * | 1/1980 | Godai et al. | 356/426 |
| 4,648,504 A | * | 3/1987 | Francioni | 198/606 |
| 4,707,251 A | | 11/1987 | Jenkins et al. | 209/569 |
| 4,747,480 A | | 5/1988 | Wedler et al. | 198/396 |
| 4,889,224 A | * | 12/1989 | Denker | 198/382 |
| 5,074,400 A | * | 12/1991 | Focke et al. | 198/415 |
| 5,249,912 A | | 10/1993 | Warga, III | 414/746.3 |
| 5,788,049 A | * | 8/1998 | Ardison | 198/408 |
| 6,172,355 B1 | * | 1/2001 | Gast et al. | 250/223 B |
| 6,236,008 B1 | * | 5/2001 | Bonnet | 209/583 |

* cited by examiner

Primary Examiner—David Porta
Assistant Examiner—Davienne Monbleau
(74) Attorney, Agent, or Firm—Thelen Reid & Priest LLP

(57) ABSTRACT

A device for controlling a continuous movement of an object with symmetry of revolution (1) comprises a conveyor (5) having two parallel guides, (6) and at least one pair of belts (8) stretched on the guides, between and on which these objects move at the level of the guides. These belts form an angle (11) between a top track and a lower track of each of the belts. The belts in the pair have the same direction of rotation around the guides, the same value of the measured angle (11) from the upper track to the lower track, and the same displacement speed. Preferably, the pair of belts consists of a single folded belt.

8 Claims, 2 Drawing Sheets

DEVICE FOR CONTINUOUS MOVEMENT OF OBJECTS WITH SYMMETRY, USE FOR VISUAL INSPECTION AND CONTROL

BACKGROUND OF THE INVENTION

The purpose of the invention is a device for continuous movement of objects with symmetry of revolution. One of the target applications is the inspection of cylindrical objects at a high speed.

Putting into movement in this case means a combined translation and rotation movement; objects rotate at the same time as they move forwards, for example to present their entire lateral surface (for example cylindrical) to sensors that will check their appearance or characteristics. It is desirable to have a device enabling a large flow of objects on a production or inspection line, by minimizing manipulations of these objects that can follow each other, very close together, in a continuous flow. Therefore, the required movement type must enable continuity of the production flow and displacement of each object at the same time. The device that satisfies this problem must guarantee uniformity of movement—which must be perfectly continuous both in translation along the main axis of the object, and in rotation about this axis—for example to enable a good quality inspection (good quality images obtained in the visual and inspection application), even at high rate, despite constraints imposed on the advance speed of the objects. The design of this type of device must be based on a simple principle, and its operation must be easy to adjust.

Conveyor belts and other conveyance devices are well known, but the need to rotate the objects at the same time as they are being translated after orienting them correctly causes special problems. The production of a system rotating and translating objects at the same time is not easy since if two different forces are to be applied to the object, the rotation and translation movements oppose each other which causes friction that reduces the smoothness of the final movement. However, there is a solution available in "centerless" grinding machine tools, that applies a rotation movement to cylindrical parts by skew applied friction. In this case, the parts also move longitudinally. But this is only possible if the parts are sufficiently long. Furthermore, there is no guarantee of the flow continuity.

This principle is repeated in some inspection systems like that patented by the Rohrer Inc Company (US) in U.S. Pat. No. 5,249,912 "Inspection apparatus" published on May 10, 1993. The double movement is then applied to the cylindrical object by means of a belt that entrains objects in rotation by friction and a double guide above and through this belt that applies a translation movement to these objects. The application divulged in this patent was an eddy currents inspection. The solution divulged in this patent consists of orienting the cylindrical objects by making them slide under an inverted channel pathway that aligns their axes with the direction of advance, and rotation is achieved by passing the objects on an endless belt that moves in a lateral direction (but not perpendicular) and forces a rolling movement on them.

Unfortunately, this system comprises limitations due to friction between objects and the guide. This friction prevents a perfectly regular helical movement at a high rate. The simultaneous rotation/translation movement imposed by the endless belt on an object that is stopped by a guide, regardless of the type of guide, necessarily generates friction between the object and the guide (inverted channel in the patent mentioned above) that disturbs the uniformity of this movement and cause jerks and vibrations on the object, particularly at high speeds. This friction and its disturbing consequences can then blur the images of the object taken with an optical detector, for example in a visual inspection. In this case, and particularly at high speeds, this device cannot produce the very high quality images necessary for a high performance inspection. Furthermore, if severely damaged parts appear, they may be entrained very irregularly, and the rotation movement would be hindered or even actually stopped. The part is then very badly entrained since apart from the fact that parasite friction affects the movement of the guide, there is only a single line of contact between the part and the belt. Finally, the space available to contain inspection sensors is reduced due to the presence of the guide (for example a simple or double rail) and may be insufficient for inspection applications using sensors other than those described in the Rohrer patent.

The device according to the invention is intended to improve the movement, and particularly to completely solve these disturbing friction problems by eliminating defects inherent to prior devices.

SUMMARY OF THE INVENTION

This invention proposes a device to apply continuous movement to objects with symmetry of revolution comprising a conveyor, characterized in that the conveyor comprises two parallel guides (such as cylinders or rounded sabres) and at least one pair of belts pulled tight on each of the guides, between and on which the objects are moving at the same level as the guides, these belts forming an angle (11) between an upper track and a lower track of each of the belts, the belts in the pair having the same direction of rotation around the guides, the same value of the measured angle (11) of the upper track to the lower track, and the same displacement speed.

To simplify the presentation, the two parallel guides covered by portions of the moving belts will be called "guide-belts" in the remainder of this presentation, to express the fact that the objects are in contact with the moving portions of the belts covering the guides but are never in direct contact with the guides themselves. Each guide-belt forms an angle α (not a right angle) with the portion of the belt that it guides; this angle depends directly on the angle 11.

The spacing between these two guide-belts is adjustable and is used to form a natural V-shape to guide objects that are entrained on both sides by the belt system both in rotation and in translation, along the axis of this natural guide. The translation/rotation ratio depends on the angle (11) and may be adjusted by a variable orientation of the belt with respect to its guide.

In this solution, there is no longer any parasite friction between the part to be entrained/inspected and an artificial guide which stops it, hindering the simultaneous rotation and translation movement due to its inherent principle. Objects are then moved uniformly, and the inspection may take place even at high rate without any jerks or vibrations. Very high quality images are obtained if a visual inspection is made.

The device according to the invention improves the entrainment of objects not only by elimination of jerks or vibrations, but also by a larger contact area, better distributed into several homokinetic areas (at least two edges of the object instead of a single contact line), between the object and the entrainment surfaces which improves the uniformity of the helical movement, even for damaged parts. Since objects are directed by the spacing between the parallel guide belts, this adjustable spacing will be chosen to optimize entrainment/guidance of objects as a function of their diameter. This spacing is chosen to be larger when the objects are larger, in order to give a better routing of the objects that will be supported more deeply in the V-shaped guide naturally formed by the two portions of the belt, and also a better entrainment by portions of belts that will have a better grip on the objects with a greater spacing.

Finally, the space available to contain arbitrary sensors or other useful devices is completely free around the objects, over more than 180 degrees around their lateral surface, since the presence of an artificial guide for the objects has completely disappeared.

According to a preferred embodiment of this movement device according to the invention, the belts in the pair belong to the same continuous loop, the lower tracks and the upper tracks being an extension of each other, the two connection tracks connecting the lower tracks and the upper tracks respectively. By this use of a single rolling belt, displacement speeds at the guide-belts are simply and reliably synchronized.

This type of inspection device is applied to optical inspection of objects by adding a light source to illuminate the object along at least one generating line, an image sensor covering the field of the generating line and possibly a sensor, for example an optical sensor that signals to the camera that an object has just been positioned in its field. This optional sensor is located on the path of the objects transverse to their displacement.

This application to optical inspection makes use of a general characteristic of the invention, which is the available space freed around the objects.

BRIEF DESCRIPTION OF THE DRAWINGS

The preferred embodiment of the invention, that is not unique, will now be described with reference to the following figures.

DETAILED DESCRIPTION OF PARTICULAR EMBODIMENTS

Figure 1:
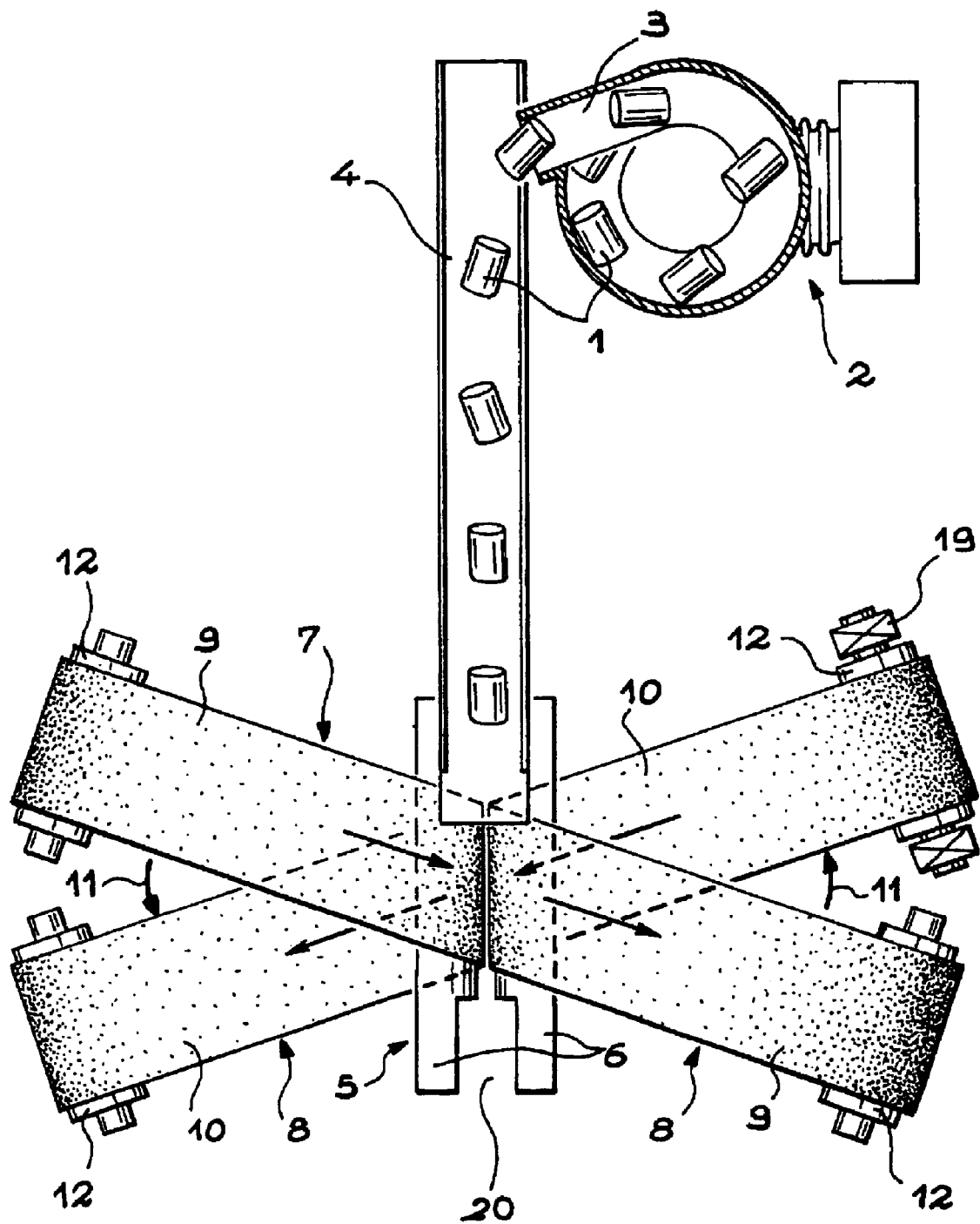
FIG. 1 is an overview of the conveyor device from the top.

Refer to FIG. 1. The objects to be moved forwards so that they can be examined may be cylindrical nuclear fuel pellets 1 originating from an arbitrary feed device (for example firstly poured into a vibrating bowl 2 and then passing along a chute 3 to fall onto an inclined gutter in which they are aligned); they arrive on the portion of the conveyor 5 associated with the optical detector (shown elsewhere) and that is specific to the invention.

The conveyor portion 5 comprises a pair of parallel guides 6 and an endless loop 7 stretched along a complex shape. It can be virtually broken down into a pair of belts 8 wound and stretched around guide-belts 6, that comprise an upper track 9 and a lower track 10 adjacent to each other on and under the guides 6. The lower track 10 and the upper track 9 are not exactly superposed but form an angle 11 between them which is the same value (in quantity and in sign) for the two belts 8, when measuring from the upper track 9 to the lower track 10 turning around a vertical axis. Furthermore, the upper tracks 9 have the same orientation and the directions of rotation of the belts 8 around their corresponding guide 6 are the same, as is clearly shown in FIG. 2. The different guide-belts have exactly the same speed without the need for a synchronization device since in this embodiment they physically form part of the same belt. The guide-belts 6 may be round bars or rounded solids such as sabres, in other words flat supports with an edge curved along a semi-circle.

The result of this is that a pellet 1 arriving on and between the two belts 8 is subjected to a joint rotation and perfectly smooth translation movement since the two upper tracks 9 move it in the same manner with the same rotation and translation speed along the guides 6. Therefore, without stopping, the pellet 1 moves successively along the portions of its side face with one detector which examines it during this time. The ratio of the rotation and movement speeds is adjusted by the value of the angle 11. A pair of rolls 12 is used for each belt 8, in order to stretch the upper track 9 and the lower track 10 around the rolls. In this embodiment, in which the belts 8 belong to a continuous loop 7, a single motor 19 driving one of the four rolls 12 is sufficient to apply the movement of the loop 7 which also includes two connection tracks 13 and 14 stretched between the pairs of rolls 12 and which connect the upper tracks 9 and the lower tracks 10 respectively together. The uniqueness of the loop 7 enables perfect synchronization of the speeds of the belts 8. The rolls 12 can be installed on supports with adjustable positions on a frame (not shown) to adjust the value of the angle 11 and the tension of the belts 8. Similarly, the spacing between the two parallel guide-belts 6 is adjustable, so that pellets can be driven/guided as well as possible as a function of their diameter. When they have gone beyond the loop 7, the pellets 1 are retracted and drop into an opening 20 formed between the guides 6. They are then retrieved by an arbitrary evacuation device not shown. Note in passing that the feed device, which may be arbitrary, could to some extent be made directly by the upper portion 8 of the belt on the upstream side of the conveyor central part, provided that the pellets are put down correctly on the belt.

The effective manufacture of a visual inspection machine using the solution consisting of the single belt with double pass providing a twofold drive of cylindrical shaped nuclear fuel pellets is a means of enabling a high inspection rate without any particular manipulation of the pellets, with very high quality images. The principle used has simplified the design of this machine and its adjustment procedures.

In the preferred application in which the positioning device is applied to a visual inspection, the detection device comprises a light source 15 directed towards the pellet 1 and that can emit a beam, preferably a plane beam, that illuminates a generating line on the pellet. The detector 16 consists of a linear strip of brightness sensors 17 connected to a camera 18. The beam of the source 15 striking the generating line 25 of the pellet 1 is returned to the detector 16 in order to form an image of this generating line, and the camera 18 compiles images of generating lines as the pellet 1 moves forwards to give a global image of it. A sensor placed in front of the path of the pellets 1 may be used to detect arrival of the pellets in the field of the detector 16 and the camera 18 and begin taking photos. These image acquisition processes are known and therefore no particular description will be given for them.

Defects of pellets 1 usually consist of dimensional errors or local surface defects such as splinters, cracks, open cavities, marks, scratches, pitting or inclusions of foreign bodies. In all cases, they produce a non-uniformity at the surface of the pellet 1. Light originating from the source 15 is directed so that it is reflected to the detector 16 when it reaches a generating line normal to the pellet 1. Otherwise, the light is returned irregularly, very much weakened, or is not close to the sensors strip 17.

There are two possible variants that affect the method used to illuminate the object.

Figure 2:
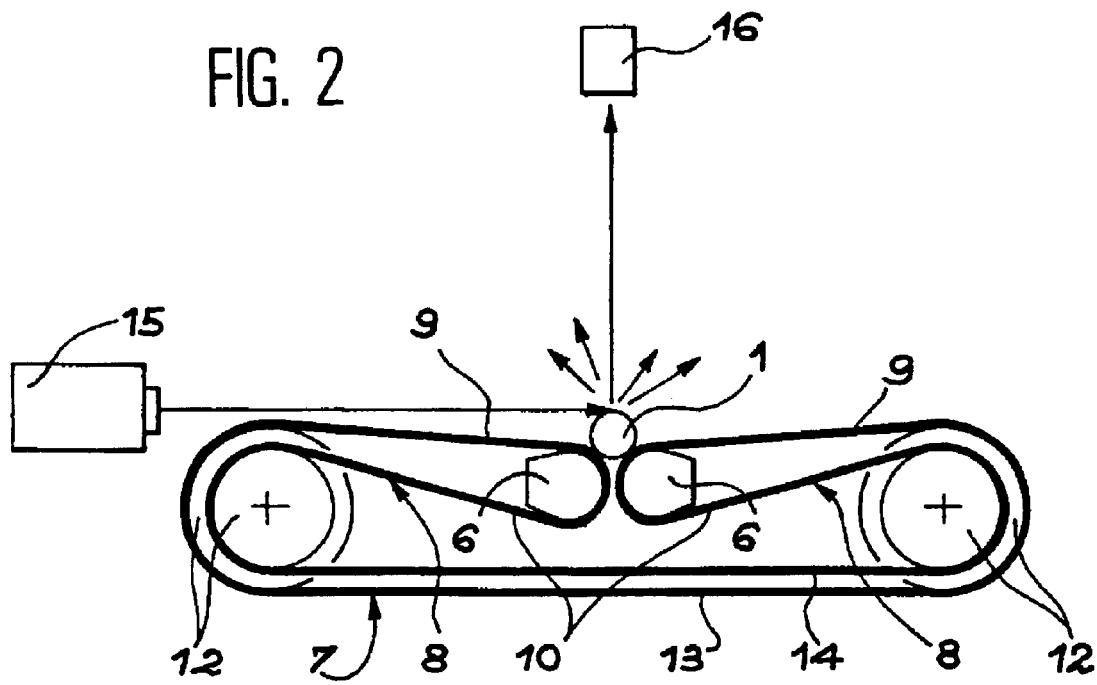
FIG. 2 is a side view of a new part of the conveyor device.
Figure 3:
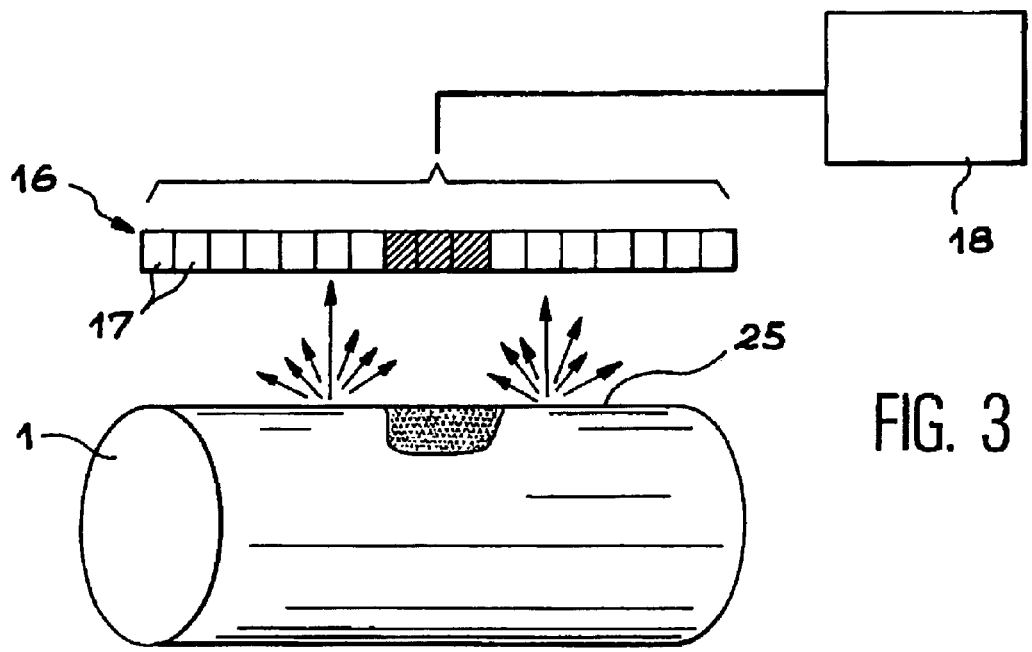
FIG. 3 illustrates an optical detector device.

According to a first variant, the light may be grazing light directed to the upper generating line of the pellet 1, as shown in FIG. 2. Under normal conditions, light is returned to the sensor strip 17 by diffusion. If there is a cavity or a crack, etc., in pellet 1, light will not be intercepted and scattered again at this location, and the corresponding sensors 17 are not illuminated. This method gives very good results but requires a powerful source (or a very sensitive camera/objective assembly) since the scattered light returned by the pellet is fairly weak. Furthermore, it must be possible to make a fine adjustment to the grazing position of the light beam.

According to a second variant, light may be directed towards an arbitrary generating line of the pellet 1 and returned by reflection. Light is reflected on a regular portion of the pellet with a maximum intensity exactly along the centreline of a well-positioned sensor, but conversely a surface defect no longer reflects the light beam along the axis of this sensor and the fault will be seen as being much darker. The advantage of this method is that it requires much less powerful lighting; furthermore, the system is easy to adjust by adjusting the position of the camera to produce a practically saturated image when the objective is fully open.

The camera (16) is synchronized on the pellets by using an optical micro-sensor operating in emission/reception, transverse to its displacement. This type of sensor is fairly well known and is not shown.

This type of device can be used for many other applications in addition to a visual inspection, such as an inspection using any other type of sensor (optical, magnetic, electrical, ultrasound, eddy current, etc.).

The system may also be applied to any process other than inspection that does not apply a large force to the object of revolution to be treated.

More generally, the device enables entrainment of arbitrarily shaped objects whenever they have symmetry of revolution (such as cylindrical, spherical objects, etc.).

What is claimed is:

1. Device for creating continuous movement of objects with symmetry of revolution (1) comprising:
   a conveyor (5);
   two parallel guides (6) extending along an end of said conveyor; and
   at least one pair of belts (8), the belts in a pair being respectively stretched over the guides, defining a path between and on which these objects travel when passing alone the guides, an angle (11) being formed between an upper track and a lower track of each of the belts, the belts in the pair having a same direction of rotation about the guides, a same value of the angle (11) from the upper track to the lower track, and a same displacement speed.

2. Device for creating continuous movement according to claim 1, wherein each of the belts in the pair forms part of a same continuous loop (7), the lower tracks (10) being in extension with each other and the upper tracks (9) being in extension with each other, the loop comprising connection tracks (13, 14), each of the connection tracks connecting the lower tracks and one of the upper track.

3. Device for creating continuous movement according to claim 1, further comprising a detector (16) consisting of a sensor or a row of sensors (17) parallel to the guides (6) and sensitive to a light reflected or scattered by the objects (1).

4. Device for creating continuous movement according to claim 3, wherein the light is grazing an upper generatrix of the object and reflected by diffusion to the row of sensors (17).

5. Device for creating continuous movement according to claim 3, wherein the light is directed towards any generatrix of the object (1) and reflected to the row of sensors (17).

6. Device for creating continuous movement according to claim 1, further comprising a sensor on the path of the objects (1) that is capable of signaling to a camera that an object has just been positioned in its field.

7. An assembly comprising the device for creating continuous movement according to claim 1, and a system (16) for detection of defects in objects (1).

8. A device for making an optical inspection of nuclear fuel pellets comprising the device for creating continuous movement according to claim 1.

* * * * *